United States Patent [19]

Brown et al.

[11] Patent Number: 4,795,806
[45] Date of Patent: Jan. 3, 1989

[54] PHOSPHOLIPID AFFINITY PURIFICATION OF FACTOR VIII:C

[75] Inventors: James E. Brown, Lafayette; Cynthia A. Cowgill, Berkeley, both of Calif.

[73] Assignee: Miles Laboratories, Inc., Elkhart, Ind.

[21] Appl. No.: 74,123

[22] Filed: Jul. 16, 1987

[51] Int. Cl.$^4$ .......................... C07K 3/18; C07K 3/20; C07K 15/14

[52] U.S. Cl. .................................. 530/383; 530/413; 530/415; 424/101

[58] Field of Search ............... 530/383, 413, 415, 381, 530/352; 424/101

[56] References Cited

U.S. PATENT DOCUMENTS

| | | | |
|---|---|---|---|
| 4,022,758 | 5/1977 | Andersson et al. | 530/413 |
| 4,397,841 | 8/1983 | Johnson | 424/101 |
| 4,411,794 | 10/1983 | Schwinn et al. | 530/301 |
| 4,461,833 | 7/1984 | Gordon | 435/183 |
| 4,508,709 | 4/1985 | Amphlett et al. | 424/101 |
| 4,578,218 | 3/1986 | Saundry et al. | 530/415 |
| 4,675,385 | 6/1987 | Herring | 530/413 |

OTHER PUBLICATIONS

Andersson et al., Thromb. Res., 23, 481–89, 1981.
Andersson et al., Biochem. J., 200, 161–167, 1981.

*Primary Examiner*—Howard E. Schain
*Assistant Examiner*—Jeff P. Kushan
*Attorney, Agent, or Firm*—David J. Aston; Pamela A. Simonton

[57] ABSTRACT

Affinity purification of Factor VIII:C, both plasma derived and genetically engineered, using coupled phosphatidylserine (PS) as the predominant phospholipid (PH) results in a high degree of purity of Factor VIII:C, similar to that previously demonstrated with monoclonal antibodies specific to either Factor VIII:C or von Willebrand factor. Phospholipids that can be used in combination with PS are phosphatidylcholine (PC) and phosphatidylethanolamine (PE).

11 Claims, No Drawings

PHOSPHOLIPID AFFINITY PURIFICATION OF FACTOR VIII:C

FIELD

This disclosure is concerned with the purification of Factor VIII:C, both plasma derived and genetically engineered and fusion products thereof. More specifically, coupled phosphatidylserine (PS) as the predominant phospholipid in affinity chromatography can be used in the purification and separation of Factor VIII to obtain a high degree of purity of Factor VIII:C.

BACKGROUND OF THE INVENTION

Factor VIII (antihemophilic factor) isolated from plasma or commercial concentrates consists of multiple polypeptides with $M_r$ approximately 80,000–210,000. Additionally, recombinant DNA clones have allowed the construction of plasmids which direct the expression of Factor VIII protein in transfected mammalian cells. Further, recombinant DNA clones have allowed the construction of plasmids which direct the expression of fusion products of Factor VIII protein in transfected mammalian cells. Factor VIII:C, as it relates to the present invention, refers to a Factor VIII protein that can function to correct the hereditary bleeding disorder termed hemophilia. Factor VIII can be from a plasma derived or genetically engineered source, or fusion products thereof. Plasma derived Factor VIII could be of human, porcine, or bovine origin and concentrates thereof. The term Factor VIII is not meant to be a limitation but refers to a functional protein for treating bleeding disorders.

A plurality of methods have been used for separating Factor VIII:C from plasma. Tuddenham et al, JOURNAL OF LABORATORY CLINICAL MEDICINE, Vol. 93, p. 40 (1979), reported a one step method for separating Factor VIII:C from most other plasma proteins using polyclonal antibodies to von Willebrand factor coupled to agarose beads. Austen, BRITISH JOURNAL OF HAEM., Vol. 43, p. 669 (1979), purified Factor VIII employing an aminohexyl-substituted agarose. Zimmerman et al, U.S. Pat. No. 4,361,509 and U.S. Pat. No. Re. 32,011, describes a method of separating the component molecules of Factor VIII/von Willebrand factor (vWf) complex using a two step procedure, (1) adsorbing a VIII:C/vWf complex onto particles bound to a monoclonal antibody specific to vWf, and (2) adsorbing the eluted VIII:C on an aminohexyl agarose column for concentration and further purification of Factor VIII:C. Purification of Factor VIII:C from genetically engineered DNA clones has been achieved by first adsorbing the Factor VIII:C onto DEAE-Sepharose, eluting Factr VIII:C and passing the material through a Factor VIII monoclonal antibody column, Gitschier et al, NATURE, Vol. 312, Nov. 22, 1984, pp. 330–337. Rotblat et al, Biochemistry, 1985, 24, 4294–4300 describe a method for purifying human Factor VIII:C from cryoprecipitate, using a polyelectrolyte procedure as a preliminary step before immunoaffinity chromatography with antibody to von Willebrand factor followed by adsorption to a monoclonal antibody specific to Factor VIII:C. To date, the most successful purifications of Factor VIII:C from plasma and recombinant DNA clones have been accomplished by using monoclonal antibodies specific to either Factor VIII:C or von Willebrand factor.

Although monoclonal antibodies have been successfully used to obtain a relatively pure Factor VIII:C preparation, monoclonal antibodies can be present in the final preparation because of leaching from the support matrix. This raises the possibility of antigenicity when the final preparation is introduced into animal systems, since murine monoclonal antibodies are not a normal metabolite and are known to be antigenic. A second disadvantage of the use of monoclonal antibodies is the requirement of cell culture facilities for producing monoclonal antibodies and the concomitant cost and handling/processing associated with monoclonal antibodies.

This invention avoids the problems associated with monoclonal antibodies yet still provides a highly purified preparation using at least one phospholipid coupled to a support structure with the predominant phospholipid being phosphatidylserine.

Binding of Factor VIII:C to phospholipid vesicles has been demonstrated using an IRMA assay, sucrose gradient ultracentrifugation and column chromatography. Lajmanovich et al, Biochimica et Biophsica Acta, 678 (1981), 132–136, investigated the interaction between purified human Factor VIII and phospholipid vesicles. An equimolor mixture of PS and PC were studied by sucrose gradient ultracentrifugation. Other experiments, not shown in the reference, referred to the use of PS or PC vesicles. The authors showed that in the presence of PS/PC or PS/PE vesicles Factor VIII activity was completely separated from vWf using sucrose-density-gradient ultracentrifugation, VIII:C appearing with phospholipids at the top and vWf migrating to the bottom.

Yoshioka et al, Brit. J. Haem., 1983, 55, 27–36, studied the interaction between Factor VIII clotting antigen (VIII:C Ag) and phospholipid (PL) using an IRMA approach. Treatment of Factor VIII concentrate with purified phospholipids showed greatest VIII:C Ag reduction with PS, less with PE and very little with PC.

Andersson and Brown demonstrated by sucrose gradient ultracentrifugation that Factor VIII/von Willebrand factor binds to phospholipid vesicles in solution (BIOCHEM. J. [1981] 200, 161–167). The phospholipid vesicles were a 50/50 mixture of phosphatidylserine and phosphatidylethonalamine (PE) or a 50/50 mixture of phosphatidylserine and phosphatidylcholine (PS). Andersson et al were also successful at coupling phospholipid vesicles containing phosphatidylserine and phosphatidylethanol amine to cyanogen bromide-activated agarose gels, (THROMBOSIS RES. 23:481–489, 1981). A 50/50 mixture of PS/PE was again used. Factor VIII/von Willebrand factor was shown to bind to the phospholipid vesicles in the absence of $Ca^{++}$ but attempts to elute any Factor VIII with 1M NaCl were unsuccessful. Factor VIII was eluted with 1M KSCN resulting in fairly low recovery of Factor VIII activity due to the lability of Factor VIII in KSCN.

A primary object of this invention is to obtain a relatively pure Factor VIII:C preparation from plasma derived or genetically engineered sources and fusion products thereof without the problems associated with monoclonal antibody purification.

Another object of this invention is to provide a purification process that can be performed in one step to purify Factor VIII:C and fusion products thereof directly from tissue culture fluids.

Yet another object of this invention is to use a phospholipid column that is predominantly phosphatidylserine, in combination with monoclonal antibodies for further purification and isolation of Factor VIII:C.

SUMMARY OF THE INVENTION

Coupled phospholipid (PL) that is predominantly phosphatidylserine (PS) provides a powerful affinity resin for purification of full-length Factor VIII:C, from plasma derived and genetically engineered sources, derivatives thereof and fusion products thereof. Coupled PL, which is predominantly PS can be used for purification of Factor VIII:C directly from crude sources such as from plasma or plasma concentrates and tissue culture fluid and from intermediate sources such as PEG Koate®, a polyethylene-glycol process for obtaining Factor VIII, or from DEAE eluates or from purer sources such as monoclonal antibody purified Factor VIII:C.

A method of preparing high purity Factor VIII:C or Factor VIII:C fusion procoagulant activity protein comprises the steps of (a) adsorbing Factor VIII:C or fusion products thereof onto a phospholipid coated support structure that is predominantly phosphatidylserine, and (b) eluting the adsorbed Factor VIII:C or fusion products thereof with a salt solution being of a sufficient concentration to elute Factor VIII:C.

DESCRIPTION OF THE PREFERRED EMBODIMENTS

The following description provides details in which embodiments of the present invention may be made and used to achieve the separation, purification and concentration of Factor VIII:C to a degree of purity and concentration comparable with that reached using monoclonal antibodies specific to Factor VIII:C or von Willebrand factor. The following description is not meant to limit the invention and variations, by those skilled in the art, would be considered to fall within the scope of this invention.

Experiments are described that demonstrate that a phospholipid column that is predominantly PS coupled to a support structure provides a powerful affinity resin for purification of Factor VIII:C. Andersson et al, supra, demonstrated that a 50/50 mixture of PS/PC or PS/PE provides such a strong affinity for Factor VIII:C that elution with a salt solution, which was not detrimental to the activity of Factor VIII:C, was unsuccessful. It is within the scope of this invention to prepare a phospholipid support structure having PS and PE or PC, wherein the amount of PE or PC is sufficient to enhance the affinity of PS without preventing the elution of Factor VIII:C or fusion products thereof with a salt solution of at least about 1.5M. The ratio is less than 50%, a preferable amount being 10–20%. By balancing the ratio of PS and PE or PC, or mixtures thereof, it might be possible to maximize the affinity of Factor VIII:C for the phospholipid support structure, adsorb the Factor VIII:C on the phospholipid support structure and wash the adsorbed Factor VIII:C with a salt solution that is sufficient to remove unwanted proteins without eluting the Factor VIII:C. Unwanted protein, include but are not limited to proteins such as fibrinogen, fibronectin or vWf from plasma derived Factor VIII:C or proteins present in the tissue culture from expressed by all lines such as baby hamster kidney (BHK) or chinese hamster ovary (CHO) proteins. The deadsorbed washed Factor VIII:C can then be eluted with a salt concentration sufficient to elute Factor VIII:C while maintaining the activity of Factor VIII:C. The salt solution in both steps may be selected from the group consisting of NaCl, $CaCl_2$, LiCl and KCl and mixtures thereof. Alternative salt solutions can be used. The factors for selecting a salt solution are ability to eluate Factor VIII:C without substantially adversely effecting any desired characteristics of Factor VIII:C. The salt solution may be the same in both steps, for example NaCl, recognizing that the concentration of the salt solution would vary between the steps. The concentration of the salt solution in the wash step being below 1M, preferably less than 0.8M. The concentration of the salt solution in the elution step being at least 1M, preferably greater than 1.5M. The concentration of salt solution can also be adjusted to be compatible with the salt concentration of the Factor VIII:C containing liquid to be processed, such as the tissue culture fluid, DEAE eluate, plasma fraction or concentrate, etc. PL support structures coupled with substantially pure PS can also be washed with the salt solution as described above. When using substantially pure PS it is advisable to evaluate the effect of the salt concentration used in the wash step to determine if Factor VIII:C is eluted with the unwanted proteins by assaying the activity of the wash eluate for Factor VIII:C. It may be necessary to lower the concentration of the wash salt solution.

PS has been coupled to glyceryl controlled pore glass (CPG) to provide an affinity resin. The use of CPG is not meant to be a limitation, other material such as preactivated resins and beads, could be used to provide a support structure for coupling to PS.

The support structure for the phospholipid column can include both natural and synthetic polymeric materials. The support structure should be capable of being coupled to a phospholipid or mixture thereof without substantially adversely affecting any desired characteristic of the Factor VIII:C to be purified such as yield, purity and activity.

In the broad practice of this invention, the physical form or macro-configuration of the column is not critical. The column is being used for affinity chromatography and surface area for contact and binding are the important features. The support structure can be used in various physical shapes including beads, flakes, discs, fibers, films, coatings e.g. on extended surface supports and sheets, tubulars or in any other unsupported structure.

In using pore glass beads as the support structure, it was noted that the binding capacity for a 3 ml column was approximately 100 units of activity per ml of gel. For a 23 ml column the binding capacity was approximately 127 $\mu$/ml. If large volumes of fluid containing Factor VIII:C are to be processed, the volume of gel would need to be adjusted accordingly. Because this purification technique is affinity chromatography versus conventional chromatography this would not require an unmanageably tall column but could readily be processed in relatively thin, large diameter, pancake-like columns. Additionally, the flat, pancake-like column would allow faster sample applications, and could be adapted for longer washes.

PS (Sigma) was coupled to glyceryl controlled pore glass (Sigma) according to the method of Roy et al, J. CHROM. 303 (1984) 225–228. PS was suspended at 5 mg/ml in 0.1M $Na(H)PO_4$, pH 7.0, 0.1M NaCl, degassed with nitrogen. and sonicated until clarified (about 3 m). eighteen micrograms of PS was mixed with 6 grams of CPG.

Tissue culture fluid containing expressed Factor VIII:C, or tissue culture fluid containing expressed Factor VIII:C which had been contacted with a DEAE-Sepharose column resulting in a DEAE concentrate, was applied to the phosphatidylserine-glycerol controlled pore glass (PS-CPG) column in a ratio of 100 U per ml gel. When purifying larger volumes of fluid containing Factor VIII, relatively thin, large diameter columns can be prepared to facilitate large scale processing. The PS-CPG column was equilibrated in 0.05M Tris, pH 7.3, 0.3M NaCl, 0.01M CaCl$_2$, 0.02% NaN$_3$ and 10% glycerol and eluted with the same buffer containing 2M NaCl. Additional PS-CPG column runs also included a wash step of 0.6M NaCl. The eluate containing Factor VIII:C was analyzed by a Factor VIII:C clotting assay, baby hamster kidney (BHK) contamination assay, Bradford protein assay and SDS-polyacrylamide gel electrophoresis.

The components for the buffer solution can be adapted to the source of the fluid containing Factor VIII:C. In the present example, 0.3M NaCl was added to buffer to avoid adjusting the salt concentration of the DEAE eluate; 0.02% NaN$_3$ is added as a bacteriocide; and this can be substituted with other well known germicidal agents, or even removed.

Table 1 illustrates the recovery of Factor VIII:C from DEAE eluates. Recombinant FVIII:C in tissue culture fluid (TCF) or in DEAE concentrate was applied to the PS-CPG in the ratio of 100 μ/ml gel. The tissue culture fluid contained from 1000–4000 U/L of expressed Factor VIII:C. The gel was washed subsequently with 0.05 imidazole pH 6.9 containing 0.15M NaCl, 0.01M CaCl$_2$ and 0.02M glycine ethyl ester; Factor VIII was eluted with the same buffer containing 0.1M CaCl$_2$. Material obtained from DEAE-Sepharose was then passed through a PS-CPG column. The results are summarized in Table 1. The results are compared to tissue culture fluid media that was adsorbed onto DEAE-Sepharose as set forth above. The material for comparison, obtained from DEAE-Sepharose was then contacted with a column containing a monoclonal antibody specific for Factor VIII:C. The column was prepared by covalently linking 2 mg Factor VIII monoclonal antibody C$_7$F$_7$ to 1 ml of Affi-gel 10 (Bio-Rad). For a detailed procedure of preparing the C$_7$F$_7$ column see the procedure of Gitschier et al, supra.

TABLE 1

Comparison of Phospholipid Column with Monoclonal Antibody Column using DEAE Eluate as the Starting Material

| Sample | Average Recovery % | Average ug BHK/4500 U of F.VIII:C | Column | Column Size | Average Specific Activity u/A$_{280}$ |
|---|---|---|---|---|---|
| A$_1$ | 56 | 9.9 | PL | 3 | NT |
| B$_2$ | 39 | 9.0 | MoAB | 5 | 6129 |
| A$_2$ | 62 | 37.9 | PL | 23 | 1319 |
| B$_2$ | 68 | 1.9 | MoAB | 22 | 6091 |

The removal of BHK contamination for samples A$_1$ and B$_2$ are comparable. The BHK contamination for the larger column A$_2$ as compared to B$_2$ demonstrated that additional washing and/or more conservative peak collection are necessary to lower the BHK contamination.

Table 2 illustrates the recovery of Factor VIII:C directly from tissue culture fluid, without adsorbing extraneous proteins using DEAE-Sepharose. The monoclonal antibody C$_7$F$_7$ column step done without the DEAE-Sepharose step has not been successful at recognizing Factor VIII:C directly from tissue culture fluid.

TABLE 2

Tissue culture fluid in a volume of 50 ml, containing 50 units of Factor VIII:C with 10% glycerol and in the presence of Ca$^{++}$.

| Sample | % Recovery | ug BHK/ml | ug BHK/4500 u |
|---|---|---|---|
| 1 | 35.7 | .018 | 83 |
| 2 | 25.5 | .0065 | 26.6 |
| 3 | 48.2 | .012 | 33.8 |
| 4 | 18.7 | | |
| Average | 32 | | 47.8 |

In the absence of Ca$^{++}$ the recovery of Factor VIII was zero percent.

The coupling procedure and column buffers as previously described were used to prepare a 23 ml PL column using PS. The column was found to have a binding capacity of 127 units of Factor VIII:C per ml of phospholipid gel. The buffers contained 0.01% Tween 80 which has a stabilizing effect on Factor VIII:C. The column was run at room temperature at 6 ml/min. using FPLC for a total time of 1 hour. The sample containing recombinant Factor VIII:C was prepared by passing the tissue culture fluid containing rFactor VIII:C over a DEAE-Sepharose column twice referred to as the 2nd DEAE eluate. The results are summarized in Table 3 below.

TABLE 3

23 ml PS-CPG Column Using a 2nd DEAE Eluate (rFVIII)

| Sample | rFVIII:C (units/ml) | Volume | Total Units | % Recovered | BHK ng/ml |
|---|---|---|---|---|---|
| A | 15.6 | 43 | 670.8 | 100 | 41700 |
| FT | 0 | 150 | — | — | 7300 |
| EL$_1$ | 7.2 | 48 | 345.6 | 57* | 53.8* |
| EL$_2$ | 1.4 | 28 | 39.2 | | |
| B | 13.7 | 144 | 1972.8 | 100 | 41700 |
| FT | 0.16 | 270 | 43.2 | 2.2 | 18900 |
| EL | 12.7 | 100 | 1270 | 64.4 | 162 |
| C | 25.2 | 144 | 3628.8 | 100 | 110700 |
| FT | 2.5 | 280 | 700 | 19.3 | 58300 |
| EL pk | 90.2 | 10 | 902 | 61.9** | 253** |
| EL rest | 11.0 | 86 | 946 | | |

\* = average for EL$_1$ and EL$_2$
\*\* = average for EL pk and EL rest
Legend: FT = flow through; EL = Eluate; pk = peak; rest = remaining eluate Additional sample sources were evaluated using a 3 ml column coupled as previously described. The same column was used to evaluate 14 samples and the column displayed excellent binding capacity for all 14 runs. Both recombinant derived Factor VIII:C and plasma derived Factor VIII:C were evaluated. The sources included tissue culture containing recombinant Factor VIII, polyethylene glycol plasma concentrate containing Factor VIII, DEAE eluate containing recombinant Factor VIII, DEAE eluate containing a fusion product of recombinant F.VIII; monoclonal antibody eluate containing rF.VIII (with and without vWf) and monoclonal antibody eluate containing plasma derived (pd) F.VIII (with and without vWf). Elution conditions were demostrated with 2M NaCl and 1 M CaCl$_2$ in the presence and absence of 0.01% Tween 80. These results are summarized in Table 4 below:

TABLE 4

Comparison of Different Sources of Factor VIII

| 2nd DEAE rF.VIII | U/ML | Volume | Total U | Recovery |
|---|---|---|---|---|
| SM | 4.70 | 4.00 | 18.8 | 100% |

TABLE 4-continued

Comparison of Different Sources of Factor VIII

| | U/ML | Volume | Total U | Recovery |
|---|---|---|---|---|
| FT | 0.00 | 12.00 | 0 | 0% |
| EL | N/D | 11.00 | N/D | N/D% |
| PEG pd F.VIII | U/ML | Volume | Total U | Recovery |
| SM | 9.10 | 4.00 | 36.4 | 100% |
| FT | 0.15 | 18.00 | 2.7 | 7.4% |
| EL | N/D | 15.00 | N/D | N/D% |
| 2nd DEAE rF.VIII | U/ML | Volume | Total U | Recovery |
| SM | 9.7 | 33.00 | 320.1 | 100% |
| FT | 0.4 | 70.00 | 28.0 | 8.7% |
| EL | 22.3 | 16.00 | 356.8 | 111.5% |
| pd F.VIII | U/ML | Volume | Total U | Recovery |
| SM | 18.5 | 0.75 | 13.9 | 100% |
| FT | 0.0 | 15.00 | 0.0 | 0% |
| EL | 2.6 | 15.00 | 39.0 | 281% |
| pd F.VIII | U/ML | Volume | Total U | Recovery |
| SM | 11.3 | 2.00 | 22.6 | 100% |
| FT | 0.0 | 15.00 | 0.0 | 0% |
| EL | 1.7 | 15.00 | 25.5 | 112% |
| SM contained Albumin | | | | |
| rF.VIII | U/ML | Volume | Total U | Recovery |
| SM | 196.0 | 0.45 | 88.2 | 100% |
| FT | 0.0 | 15.00 | 0.0 | 0% |
| EL | 4.6 | 15.00 | 69.0 | 78.3% |
| SM contained Albumin | | | | |
| rF.VIII | U/ML | Volume | Total U | Recovery |
| SM | 163.1 | 0.52 | 84.8 | 100% |
| FT | 0.0 | 15.00 | 0.0 | 0% |
| EL | 3.2 | 15.00 | 48.0 | 59.6% |
| SM contained Albumin and vWf | | | | |
| pd F.VIII | U/ML | Volume | Total U | Recovery |
| SM | 11.0 | 2.00 | 22.0 | 100% |
| FT | 0.0 | 15.00 | 0.0 | 0% |
| EL | 3.0 | 15.00 | 46.5 | 211.4% |
| SM contained Albumin and vWf | | | | |
| PEG pd F.VIII | U/ML | Volume | Total U | Recovery |
| SM | 9.4 | 18.60 | 174.8 | 100% |
| FT | 1.4 | 50.00 | 70.0 | 40% |
| EL | 1.9 | 15.00 | 28.5 | 16% |
| 2nd DEAE rF.VIII | U/ML | Volume | Total U | Recovery |
| SM | 13.7 | 10.00 | 137.0 | 100% |
| FT | 0.8 | 30.00 | 22.8 | 16.6% |
| EL | 4.6 | 15.00 | 69.0 | 50.4% |
| 2nd DEAE r.F.VIII | U/ML | Volume | Total U | Recovery |
| SM | 13.7 | 10.00 | 137.0 | 100% |
| FT | .19 | 27.00 | 5.1 | 3.7% |
| EL | 7.6 | 15.00 | 114.0 | 83% |
| Eluted with 1 M CaCl₂ instead of 2 M NaCl. | | | | |
| 2nd DEAE rF.VIII | U/ML | Volume | Total U | Recovery |
| SM | 13.7 | 10.00 | 137.0 | 100% |
| FT | .22 | 27.00 | 5.9 | 4.3% |
| EL | 5.5 | 15.00 | 82.5 | 60.2% |
| 2nd DEAE rF.VIII | U/ML | Volume | Total U | Recovery |
| SM | 13.7 | 10.00 | 137.0 | 100% |
| FT | 0.45 | 27.00 | 12.0 | 8.9% |
| EL | 8.0 | 15.00 | 120.0 | 87.6% |
| Buffer contained 0.01% Tween 80. | | | | |
| 2nd DEAE rF.VIII | U/ML | Volume | Total U | Recovery |
| SM | 13.7 | 10.00 | 137.0 | 100% |
| FT | 0.36 | 27.00 | 9.7 | 7.1% |
| EL | 5.0 | 15.00 | 75.0 | 54.7% |

SM = Starting material
FT = Flow thru
EL = Eluate
Elution Buffer contained glycerol The procedure for purification of genetically engineered Factor VIII:C is different from that of plasma derived Factor VIII:C because of the presence of large protein molecules in plasma such as fibronectin and fibrinogen and the fact that Factor VIII:C is a part of the VIII:C:vWf complex. Although it has been demonstrated that Factor VIII:C can be purified by PL in the presence of vWP, large protein molecules can be removed prior to or after processing with PL. Steps for removal of these unwanted proteins are well known. These steps have been used in conventional processing of plasma to obtain lower purity Factor VIII:C, as well as in combination with monoclonal antibodies to obtain highly purified Factor VIII:C. Plasma and plasma concentrates can be pretreated to remove unwanted proteins using DEAE-Sepharose. The VIII:C:vWf complex can be disassociated with β-mercaptoethanol (BME) or CaCl₂, for example 250 mM and contacted with a DEAE-Sepharose column to remove vWf. The DEAE-eluate can then be adsorbed on the phospholipid column as set forth above.

Given the above disclosures, variations will undoubtedly occur to those skilled in the art. Accordingly, it is intended that the above examples should be construed as illustrative only and that the scope of the inventions disclosed should be limited only by the following claims.

We claim:

1. A method for preparing high purity protein having Factor VIII:C procoagulant activity comprising the steps of
    (a) adsorbing Factor VIII:C onto a rigid support to which has been coupled phospholipids selected from the group consisting of phosphatidylserine, phosphotidylcholine, and phosphotidylethanolamine, said phosphotidylethanolamine or phosphotidylcholine being present in amounts between 10% and 20% of said phospholipid, and
    (b) eluting the adsobed Factor VIII:C or fusion products thereof with a non-denaturing salt solution, said non-denaturing salt solution being of a sufficient concentration to elute Factor VIII:C while maintaining the activity of Factor VIII:C.

2. The method of claim 1 wherein said Factor VIII:C is obtained from a plasma derived source.

3. The method of claim 1 wherein said Factor VIII:C is obtained from a genetically engineered source.

4. The method of claim 2 wherein said plasma derived source includes human plasma, porcine plasma, bovine plasma, plasma concentrates and plasma fractions thereof.

5. The method of claim 1 wherein the concentration of said salt solution is at least about 1M.

6. The method of claim 1 wherein said salt solution is selected from the group consisting of NaCl, CaCl₂, LiCl and KCl.

7. The method of claim 1 further including the step of
    (a) (i) eluting the adsorbed Factor VIII:C from step (a) with a salt solution, said salt solution being of a sufficient concentration to remove unwanted contaminants without eluting said Factor VIII:C.

8. The method of claim 7 wherein the concentration of said salt is less than 1M.

9. The method of claim 7 wherein said salt solution in said step (a)(i) is selected from the group consisting of NaCl, CaCl$_2$, LiCl and KCl.

10. The method of claim 7 wherein said salt solution in step (a) (i) and salt solution in step (b) are both NaCl.

11. The method of claim 1 further comprising the step of re-adsorbing Factor VIII:C onto said support after eluting reviously adsorbed Factor VIII.

* * * * *